Nov. 1, 1955 F. W. ANDERSON Plant Pat. 1,427
NECTARINE TREE
Filed Feb. 4, 1955
Fig. 1
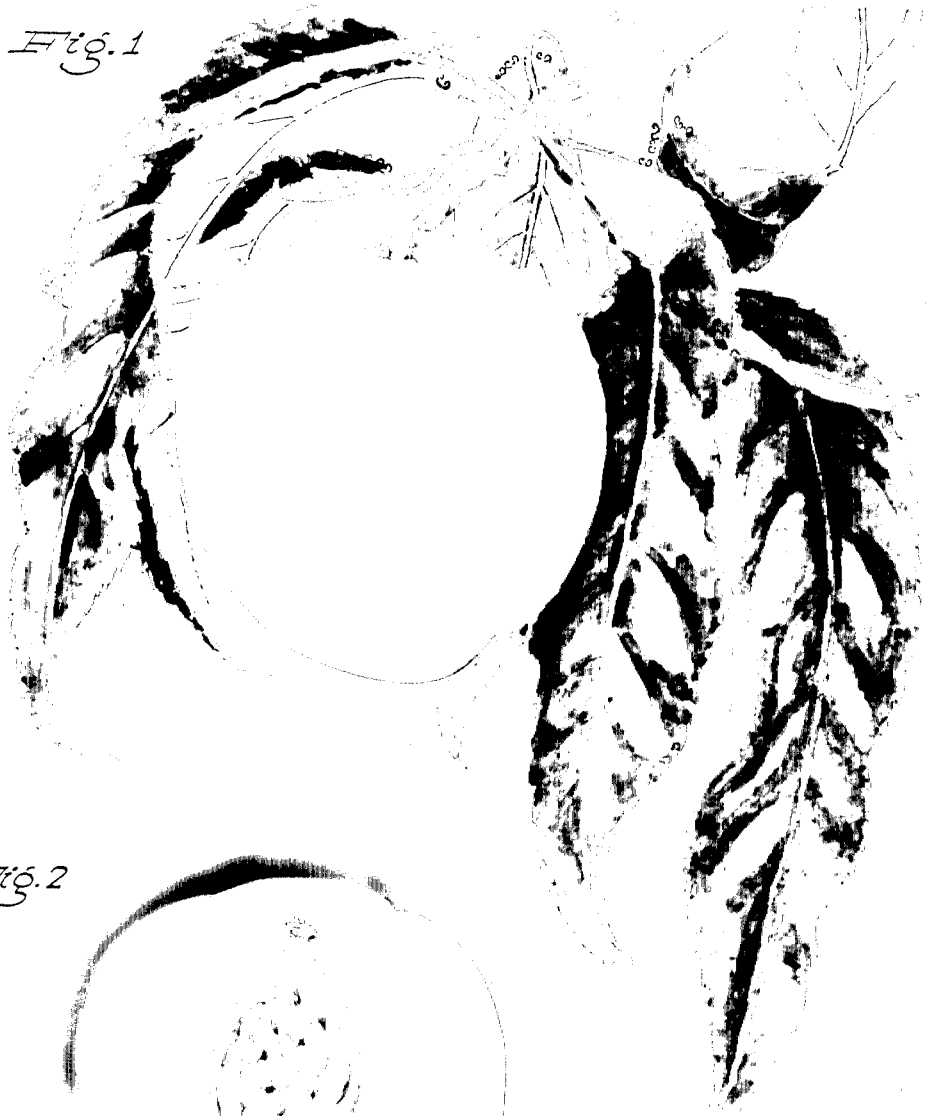
Fig. 2
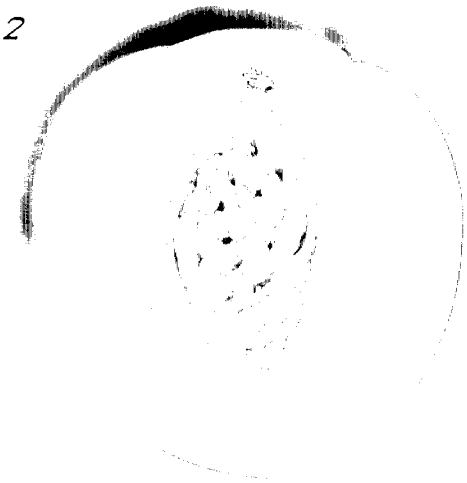
Fig. 3
WITNESS
Addison E. Avery
INVENTOR
Frederic W. Anderson
Webster & Webster
ATTYS.

United States Patent Office

Plant Pat. 1,427

Patented Nov. 1, 1955

1,427

NECTARINE TREE

Frederic W. Anderson, Merced, Calif., assignor to John M. Garabedian, Fresno, Calif.

Application February 4, 1955, Serial No. 486,305

1 Claim. (Cl. 47—62)

This invention relates to a new and distinct variety of nectarine tree which bears yellow fleshed freestone fruit of desirable market quality; the fruit being of yellow exterior color overspread with red to a substantial extent.

The present variety of nectarine tree is a cross between the Le Grand nectarine (United States Plant Patent 549) and an unnamed seedling of the Bim nectarine (United States Plant Patent 575); the variety having been originated by me during a continuing fruit variety development and testing program conducted in my experimental nursery and orchard at Le Grand, Merced County, California.

When the original plant of the variety, which was maintained under close observation, came into bearing I recognized that the fruit had certain distinctive and commercially advantageous characteristics in comparison to certain other nectarines.

The present variety was therefore selected by me for reproduction, and it was successfully reproduced in my experimental nursery and orchard, as aforesaid, by top working—specifically budding—on mature orchard trees. The asexual reproductions of the variety were found to run true in all respects relative to the parent.

The major distinctive characteristics of the present variety of nectarine tree, especially by reference to the fruit, will be evident from the following:

As compared to the Sun Grand nectarine (United States Plant Patent 974) the present variety bears fruit which is of slightly larger average size, ripens approximately one week earlier, is softer, and is of better quality.

As compared to the John Rivers nectarine (unpatented) the fruit of the present variety ripens approximately one week later, has yellow instead of white flesh, and is a freestone instead of a semi-cling.

In the drawings:

Fig. 1 is a perspective view of one of the fruit, together with twigs and leaves.

Fig. 2 is a sectional elevation of one of the fruit with the stone exposed.

Fig. 3 is a fragmentary elevation of a leaf.

Referring now more specifically to the pomological details of this new and distinct variety of nectarine tree, the following is an outline description thereof; all major color plate identifications being by reference to Maerz and Paul Dictionary of Color:

Tree:
- *Size.*—Medium.
- *Vigor.*—Vigorous.
- *Growth.*—Spreading.
- *Density.*—Open.
- *Production.*—Productive.
- *Bearer.*—Regular bearer.

Trunk:
- *Size.*—Medium.
- *Surface.*—Medium.

Branches:
- *Size.*—Medium.
- *Surface.*—Medium.
- *Lenticels.*—Number—medium.

Leaves:
- *Size.*—Medium. Average length—6¼"; average width—1⅜".
- *Thickness.*—Medium.
- *Color.*—Top side—medium green (22–L–8). Under side—lighter green (22–K–6).
- *Margin.*—Crenate.
- *Petiole.*—Medium length; medium thickness.
- *Glands.*—Average number—four. Position—usually two or three on petiole and at least that many on blade.
- *Stipules.*—None.

Flower buds:
- *Size.*—Medium.
- *Length.*—Medium.

Flowers:
- *Dates of first and full bloom.*—Usually two or three days before the Elberta peach (unpatented).
- *Size.*—Large.

Fruit:
- *Maturity when described.*—Eating ripe.
- *Date of first picking.*—July 3, 1954.
- *Date of last picking.*—July 10, 1954.
- *Size.*—Uniform; medium. Average diameter axially—2½". Average transverse in suture plane—2 9/16".
- *Form.*—Uniform; symmetrical; globose.
- *Suture.*—An inconspicuous line; shallow. Slight depression beyond pistil point.
- *Ventral surface.*—Rounded strongly; lips equal.
- *Cavity.*—Rounded. Average depth—7/16"; average breadth—9/16".
- *Base.*—Rounded.
- *Apex.*—Short.
- *Pistil point.*—Very small.

Skin:
- *Texture.*—Medium thickness; medium tender.
- *Tendency to crack.*—None in wet season.
- *Down.*—Wanting.
- *Color.*—Yellow (9–L–3 shading to 9–J–7), overspread to a substantial extent with red (4–L–12) in the portion adjacent the apex, and which shades to an orange cast (11–L–12) in the direction of the base.

Flesh:
- *Juice.*—Abundant; rich.
- *Texture.*—Medium to soft; melting.
- *Fibers.*—Few.
- *Ripens.*—Even.
- *Flavor.*—Delicate; vinous.
- *Aroma.*—Distinct.
- *Eating quality.*—Good to best.
- *Color.*—Yellow (9–L–3 shading to 9–K–6), mottled and slightly streaked with red (3–L–3) next to stone; slight mottling of red next to skin toward apex.
- *Surface of pit cavity.*—Reddish pink.

Stone:
- *Type.*—Free. Parts from flesh smoothly.
- *Size.*—Small. Average length—1¼"; average breadth—1 1/16"; average thickness—⅞".
- *Form.*—Obovoid.
- *Base.*—Straight.
- *Hilum.*—Narrow; oblong.
- *Apex.*—Rounded.
- *Sides.*—Equal.
- *Surface.*—Regularly furrowed throughout; ridged throughout; pitted toward base.

*Ridges.*—Rounded.
*Pits.*—Angular.
*Ventral edge.*—Thick.
*Dorsal edge.*—Full.
*Tendency to split.*—Slight.
*Color.*—Tan with greenish cast (13–K–7), with a darker olive green shading on the ridges, with a pink cast bordering in the pits.

Use: Market; local; dessert.
Keeping quality: Medium.
Shipping quality: Medium.

The tree and its fruit herein described may vary in slight detail due to climatic and soil conditions under which the variety may be grown.

The following is claimed:

A new and distinct variety of nectarine tree, as illustrated and described, which bears medium sized, yellow fleshed, freestone fruit having a yellow exterior color overspread to a substantail extent with red, and characterized—in comparison to the Sun Grand nectarine—by fruit averaging slightly larger in size, ripening approximately one week earlier, softer in flesh, and of better eating quality; and characterized—in comparison to the John Rivers nectarine—by fruit which ripens approximately one week later, having yellow instead of white flesh, and being a freestone instead of a semi-cling.

No references cited.